(12) United States Patent
Folchini et al.

(10) Patent No.: US 8,925,723 B2
(45) Date of Patent: Jan. 6, 2015

(54) PACKAGE FOR PHARMACEUTICAL PRODUCTS

(75) Inventors: Enrico Folchini, Rho (IT); Tullio Cottignoli, Cervia (IT)

(73) Assignee: Essentra Packaging S.R.L. (IT)

( * ) Notice: Subject to any disclaimer, the term of this patent is extended or adjusted under 35 U.S.C. 154(b) by 0 days.

(21) Appl. No.: 13/696,967

(22) PCT Filed: May 10, 2011

(86) PCT No.: PCT/IB2011/052055
§ 371 (c)(1),
(2), (4) Date: Nov. 8, 2012

(87) PCT Pub. No.: WO2011/141871
PCT Pub. Date: Nov. 17, 2011

(65) Prior Publication Data
US 2013/0062245 A1    Mar. 14, 2013

(30) Foreign Application Priority Data

May 11, 2010 (IT) ............................... BO2010A0300

(51) Int. Cl.
*B65D 83/10* (2006.01)
*B65D 25/04* (2006.01)
(Continued)

(58) Field of Classification Search
CPC .... A61B 10/0096; A61B 19/02; A61F 17/00; A61J 1/00; A61M 25/002; B65D 5/4204; B65D 5/4802; B65D 5/5007; B65D 5/5019
USPC ......... 206/363, 364, 438, 569–572, 775, 779, 206/781–783, 370; 229/120.08, 120.13, 229/120.14
See application file for complete search history.

(56) References Cited

U.S. PATENT DOCUMENTS 1,892,879 A * 1/1933 Florea et al. ............. 229/120.14
2,289,236 A * 7/1942 Broderick ..................... 206/782
(Continued)

FOREIGN PATENT DOCUMENTS

CN    2131826    5/1993
CN    1379723    11/2002
(Continued)

OTHER PUBLICATIONS

Office Action issued Oct. 17, 2013 from European Patent Office for counterpart European patent Application No. 11 723 697.6.
(Continued)

*Primary Examiner* — Bryon Gehman
(74) *Attorney, Agent, or Firm* — Timothy J. Klima; Shuttleworth & Ingersoll, PLC

(57) ABSTRACT

A package for pharmaceutical products, in particular for parenteral products (prefilled syringes, flacons, ampoules, vials, bottles), comprises a supporting body forming at least one compartment for containing a parenteral product made from a single-sheet blank, preferably made of paper-based material, which has a base face, an upper face and a plurality of lateral faces which are connected to the base face and/or to the upper face, said upper face having at least one opening made in it and comprising at least one foldable portion defined by cutting lines of the upper face and/or by crease lines and delimiting a portion of the opening to form a cavity designed to receive the parenteral product, the supporting body being able to switch between a non-operating condition in which it has a planar profile which minimises its dimensions, and an operating condition in which: the supporting body is substantially box-shaped; the foldable portion is folded inside the supporting body so that together with the opening it forms the compartment for containing the parenteral product and allows the parenteral product to be removably constrained in the cavity in the containment compartment.

21 Claims, 7 Drawing Sheets

(51) Int. Cl.
  *B65D 25/54* (2006.01)
  *B65D 5/54* (2006.01)
  *A61M 5/00* (2006.01)
  *B65D 5/42* (2006.01)
  *B65D 5/50* (2006.01)
  *B65D 71/72* (2006.01)
  *B65D 85/42* (2006.01)

(52) U.S. Cl.
  CPC ............ *B65D 5/5495* (2013.01); *A61M 5/002* (2013.01); *A61M 5/008* (2013.01); *B65D 5/4279* (2013.01); *B65D 5/5007* (2013.01); *B65D 71/72* (2013.01); *B65D 85/42* (2013.01); *B65D 2101/00* (2013.01)
  USPC ........... 206/364; 206/370; 206/782; 206/783; 229/120.14

(56) References Cited

U.S. PATENT DOCUMENTS

| | | | |
|---|---|---|---|
| 3,292,777 A * | 12/1966 | Desmond | 206/779 |
| 3,675,763 A * | 7/1972 | Sandel | 206/775 |
| 4,089,457 A | 5/1978 | Wood | |
| 4,214,659 A * | 7/1980 | Jaeschke et al. | 229/120.13 |
| 4,264,006 A * | 4/1981 | Swanberg | 206/783 |
| 4,469,271 A * | 9/1984 | Kulig | 229/120.14 |
| 4,913,339 A | 4/1990 | Elder | |
| 6,746,744 B1 | 6/2004 | Ishihara et al. | |
| 7,317,573 B2 * | 1/2008 | Billen | 359/474 |
| 2006/0158733 A1 | 7/2006 | Billen | |

FOREIGN PATENT DOCUMENTS

| | | |
|---|---|---|
| DE | 8907594 | 11/1989 |
| DE | 9100796 | 4/1991 |
| FR | 1177518 | 4/1959 |

OTHER PUBLICATIONS

Office Action issued Sep. 29, 2013 from Chinese Patent Office for counterpart Chinese patent Application No. 201180023342.X.
International Search Report and Written Opinion dated Oct. 10, 2011 from counterpart application.

* cited by examiner

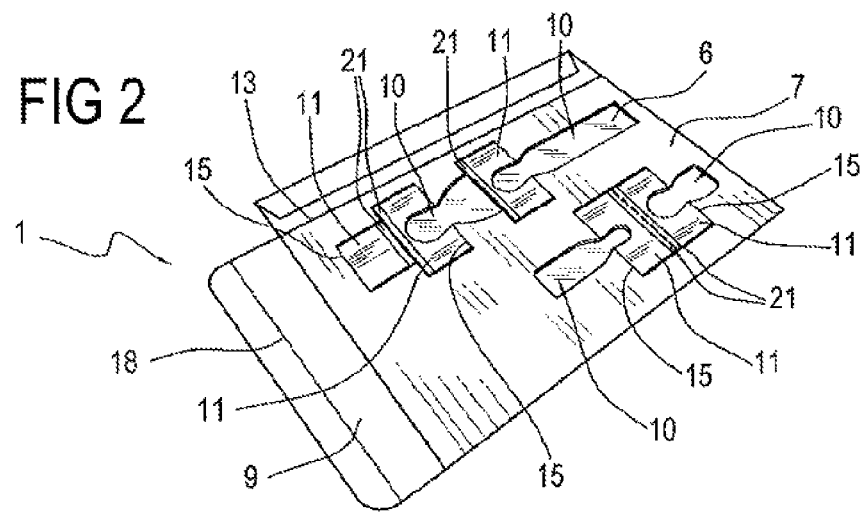
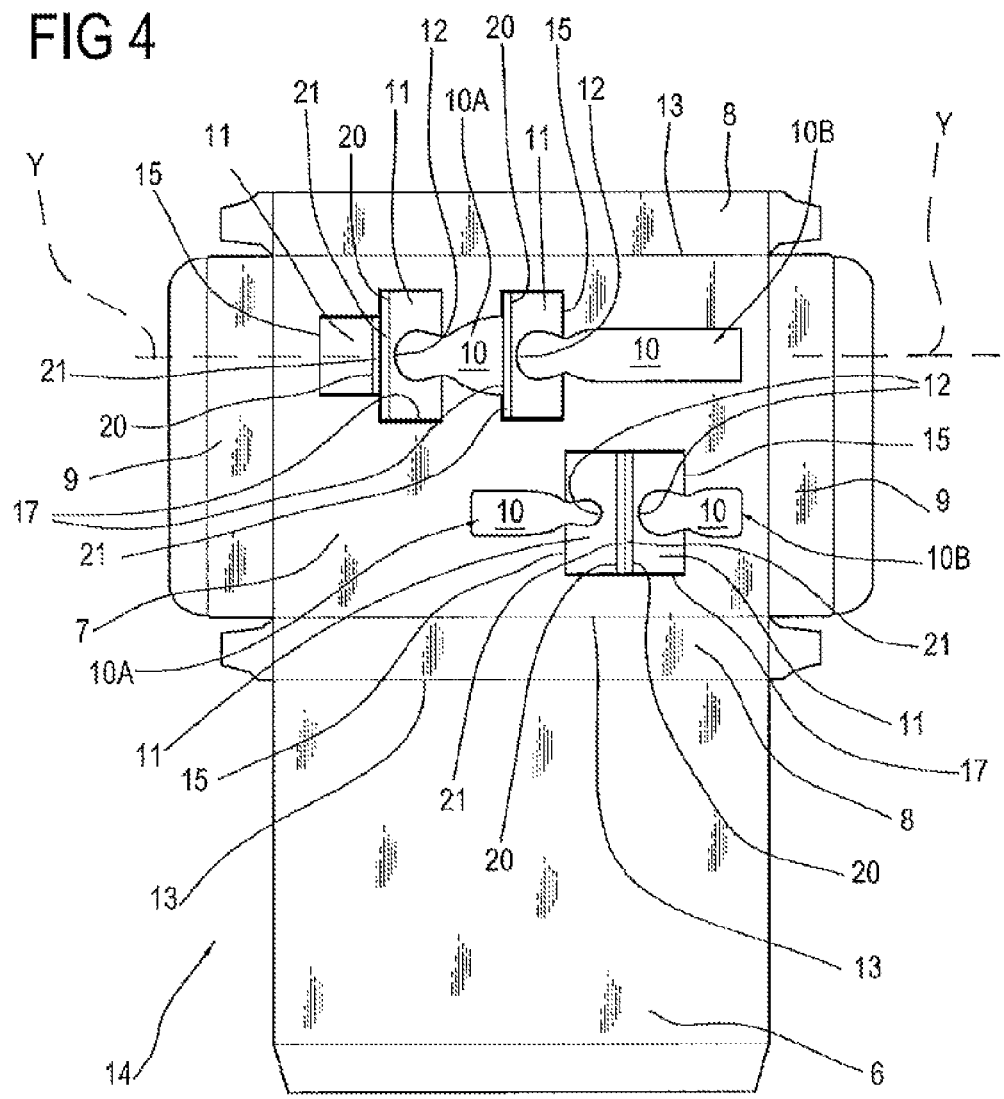

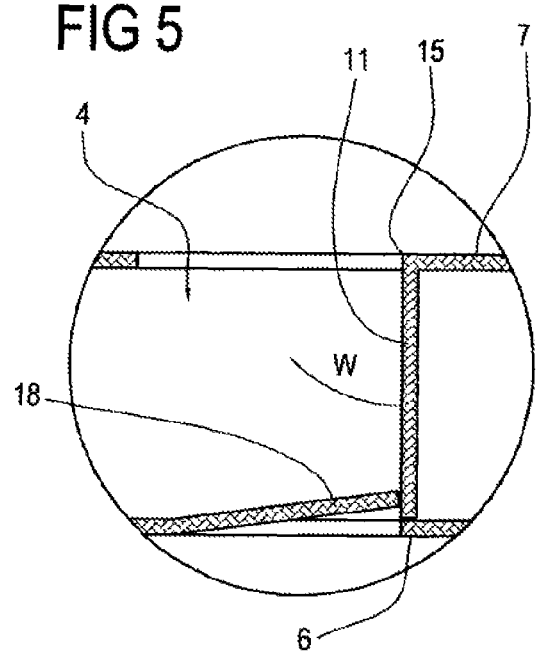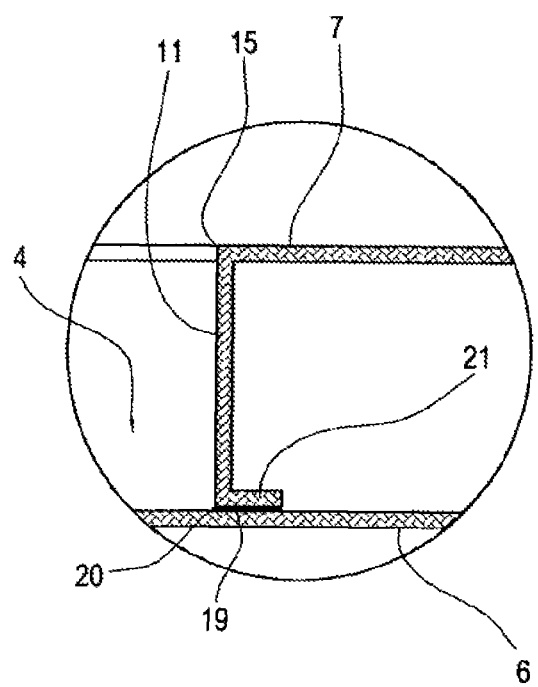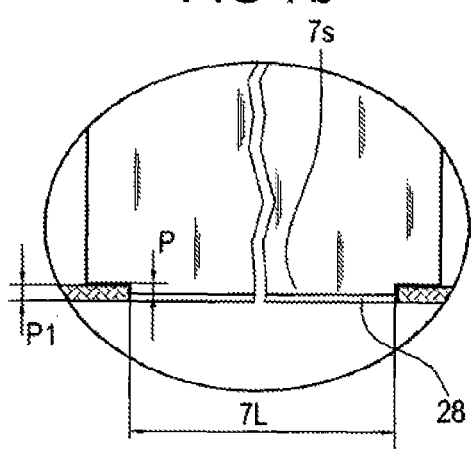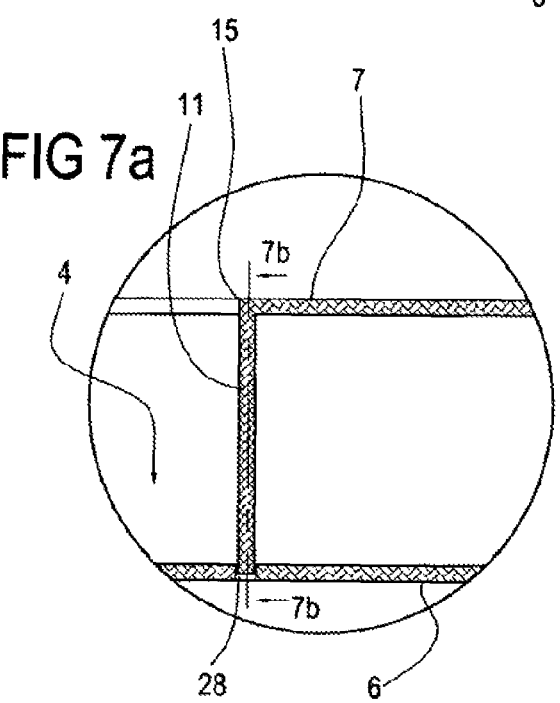

PACKAGE FOR PHARMACEUTICAL PRODUCTS

This application is the National Phase of International Application PCT/IB2011/052055 filed May 10, 2011 which designed the U.S. and that International Application was published under PCT Article 21 (2) in English.

This application claims priority to Italian Patent Application No. BO2010A000300filed May 11, 2010 and PCT Application No. PCT/IB2011/052055 filed May 10, 2011, which applications are incorporated by reference herein.

TECHNICAL FIELD

This invention relates to a package for pharmaceutical products, in particular for parenteral products such as prefilled disposable syringes, flacons, ampoules, vials, bottles containing pharmaceutical products.

In more detail, this invention relates to a package for parenteral products, which are preferably predosed, that is to say, already filled with a suitable substance or respective medicine.

BACKGROUND ART

In one of the possible solutions, in which the parenteral products are prefilled disposable syringes, they may be accompanied by an ampoule containing the medicine in liquid or powder form which must be inserted in the syringe.

As is known, packages for pharmaceutical products consist of paperboard boxes in which a container made of plastic material is inserted. The package comprises suitable cavities for containing the pharmaceutical products.

For example, the containers may have a cavity for receiving a parenteral product, suitably shaped for retaining the product in the package. There are also prior art packages/containers which have a plurality of cavities, each designed to contain a respective product, such as a glass ampoule or a syringe.

As indicated above, each cavity is suitably shaped and has undercuts for stably positioning—lodging the object in the cavity and at the same time for allowing it to be removed manually from the package.

Such packages made of plastic material are usually made using thermoforming processes, designed to give the container its box-shaped outline. During the thermoforming process the containment cavities for the syringes and/or ampoules are also made in the upper surface of the box-shaped outline.

In this way, according to the dimensions and outline of the pharmaceutical products to be packaged, suitably sized plastic containers are produced.

However, the packages described above, although able to contain any type of disposable product, have significant disadvantages.

First, it should be noticed that, if the packages are not made immediately before they are used, their dimensions are such that they occupy an excessive amount of storage space.

Such dimensions are due to the box shape of the packages which, even during the production and packaging steps, are particularly bulky.

Another disadvantage is caused by the methods for thermoforming the package, which require the use of special, expensive and structurally complex machines, as well as the use of polymeric materials which by definition are not considered environmentally friendly.

Document US 2006/158733 describes a carton for containing food or beverages.

The carton has openings equipped with tabs which can be folded inwards.

The products are placed in the openings. It should be noted that placing the products in the opening causes the tabs to be folded inwards.

The purpose of the foldable tabs is basically that of laterally containing the products; it should be noted, however, that this does not prevent the products from falling if the carton is tilted and/or turned upside down.

Thus, one disadvantage of this type of package is that of not guaranteeing a sure and secure hold on the products inside the openings.

Patent document DE 8907594 describes a package having an intermediate bottom.

The package comprises a compartment equipped with lateral tabs which can be folded inwards.

The tabs form side walls of the compartment to allow the product to be laterally contained when it is placed in the compartment. With this type of package, too, the product is not held securely in place, especially if the package is turned upside down and/or tilted.

Another disadvantage of this type of package is due to the impossibility of automating the process of erecting the package from a flat non-operating configuration (suitable for storage) to a box-shaped operating configuration (suitable for use). Indeed, the process involves a plurality of folding steps which are difficult to automate.

Patent document U.S. Pat. No. 4,913,339 describes a carton for bottles, comprising a pair of compartments where each compartment is designed to accommodate a bottle.

The carton comprises a tab, associated with each compartment and designed to be folded inwards to allow the compartment to be opened.

These compartments apply on the bottles an action of laterally delimiting the compartment.

In this case too, the products are not held securely inside the carton.

In this context, the technical purpose which forms the basis of this invention is to propose a package for pharmaceutical products, in particular for parenteral products, which overcomes the above-mentioned disadvantages of the prior art.

In particular, this invention aims to provide a package for pharmaceutical products which is able to limit the dimensions of the package during the respective production, storage and packaging steps.

A further aim of the invention is to provide a package for pharmaceutical products that is particularly simple and which allows the products to be held securely and effectively inside the package even if the latter is turned upside down and/or tilted.

A yet further aim of the invention is to propose a package for pharmaceutical products which is structurally simple and easy to produce and which uses existing technologies and environmentally friendly materials, in particular new or recycled paperboard.

Another aim of this invention is to propose a solution comprising an tamper-evident system obtained with the addition of a material that is preferably paper or plastic, which indicates when the product contained in the package has been used.

DISCLOSURE OF THE INVENTION

The technical purpose indicated and the aims specified are substantially achieved by a package for pharmaceutical products comprising the technical features described in one or more of the appended claims.

In particular, the above-mentioned aims are achieved with a package for pharmaceutical products, in particular for parenteral products, comprising a supporting body forming at least one compartment for containing a pharmaceutical product and characterised in that the supporting body is made from a single-sheet blank, preferably made of paper-based material, which has a base face, an upper face and a plurality of lateral faces which are connected to the base face and/or to the upper face, said upper face having at least one opening made in it and comprising at least one foldable portion defined by cutting lines of the upper face and/or by crease lines and delimiting a portion of the opening to form a cavity designed to receive the parenteral product, the supporting body being able to switch between a non-operating condition in which it has a planar profile which minimises its dimensions, and an operating condition in which: the supporting body is substantially box-shaped; the foldable portion is folded inside the supporting body so that together with the opening it forms the compartment for containing the pharmaceutical product and allows the pharmaceutical product to be removably constrained in the cavity in the containment compartment.

The package obtained in this way is extremely simple. At the same time as the opening is made in the upper face, the cavity for retaining the product in the containment compartment is also made.

The cavity of the foldable portion is formed by a portion of the edge of the opening, said portion of the edge, when the supporting body has a planar profile, being shared both by the opening and the foldable portion.

This means that with a simple, rapid operation both the opening and the cavity for retaining the product in the compartment can be made in the blank, that is to say, this allows the access opening and the cavity for retaining the product to be made simultaneously. Therefore, advantageously the solution proposed is extremely simple and inexpensive compared with the prior art solutions described.

Moreover, the fact that the package is obtained from a single-sheet blank is extremely advantageous because it allows the package production process to be easily automated, avoiding gluing together separate component parts to form the package and limiting gluing to different portions of the same package.

BRIEF DESCRIPTION OF THE DRAWINGS

Additional features and advantages of this invention are more apparent in the non-limiting description of a preferred embodiment of a package for pharmaceutical products, as shown in the accompanying drawings in which:

FIG. 2 is a perspective view of the package of FIG. 1 in a respective non-operating condition;

FIG. 4 is a top plan view of a blank used to obtain the package illustrated in FIG. 1;

FIG. 5 is a cross-section of a detail of an alternative embodiment of the package in accordance with this invention;

FIG. 6 is a cross-section of a detail of another alternative embodiment of the package;

FIG. 7a is a cross-section of a detail of another alternative embodiment of the package, whilst FIG. 7b is a cross-section according to the line 7b-7b in FIG. 7a;

DETAILED DESCRIPTION OF THE PREFERRED EMBODIMENTS OF THE INVENTION

Figure 1:
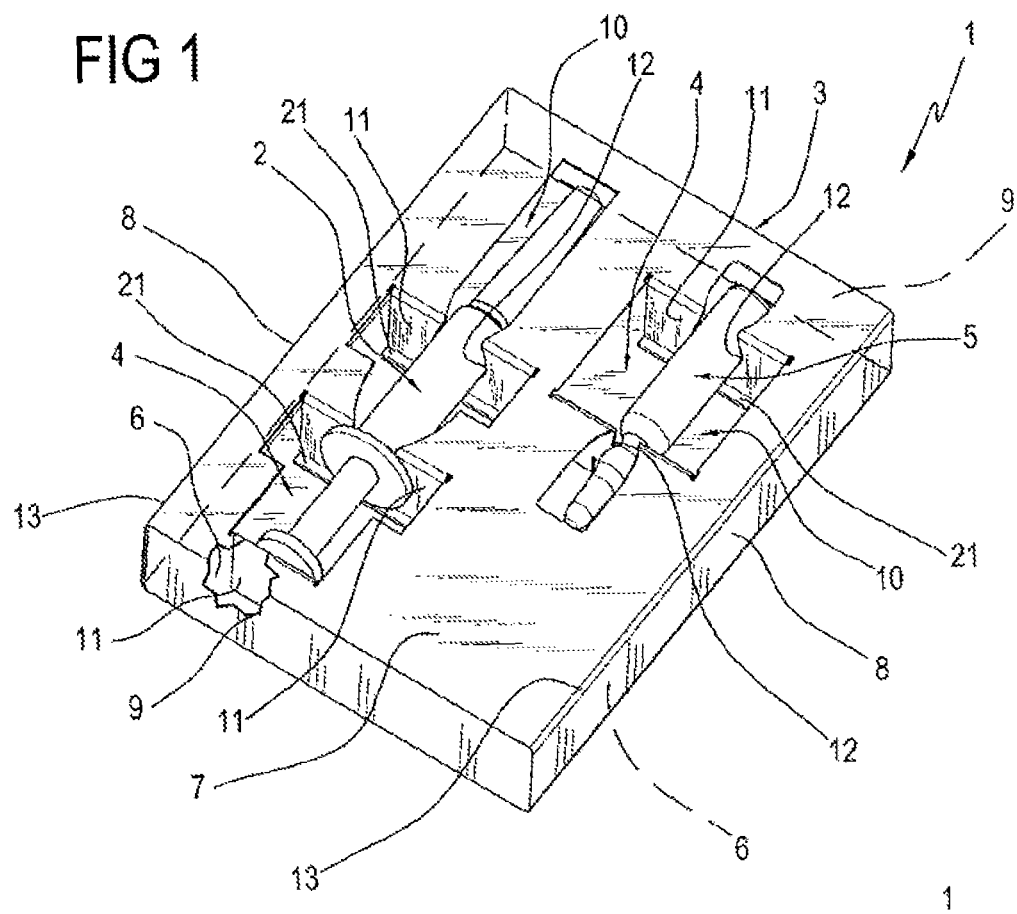
FIG. 1 is a perspective view of a package for pharmaceutical products in accordance with this invention and in a respective operating condition.

With reference to the accompanying drawings, the numeral 1 denotes as a whole a package for pharmaceutical products, in particular for parenteral products.

This invention relates specifically to packages 1 for containing parenteral products, such as, but without limiting the scope of the invention, syringes 2 or ampoules 5 containing medicines.

The term "parenteral" products refers for example to: flacons, ampoules, vials, bottles and syringes which are prefilled or to be filled.

However, this invention may be used for any type of pharmaceutical product, in particular for disposable articles, which are therefore designed to be easily disposed of and recycled if necessary.

The package 1 comprises a supporting body 3 forming at least one compartment 4 for containing a respective syringe 2.

As shown in particular in FIG. 1, by way of example but without limiting the scope of the invention, the supporting body 3 has two compartments 4, for containing respectively a syringe 2 and an ampoule 5 filled with a medicine.

The number of compartments 4 may in any case be decided according to the type of package 1 and according to the number of products which must be packaged.

Figure 3:
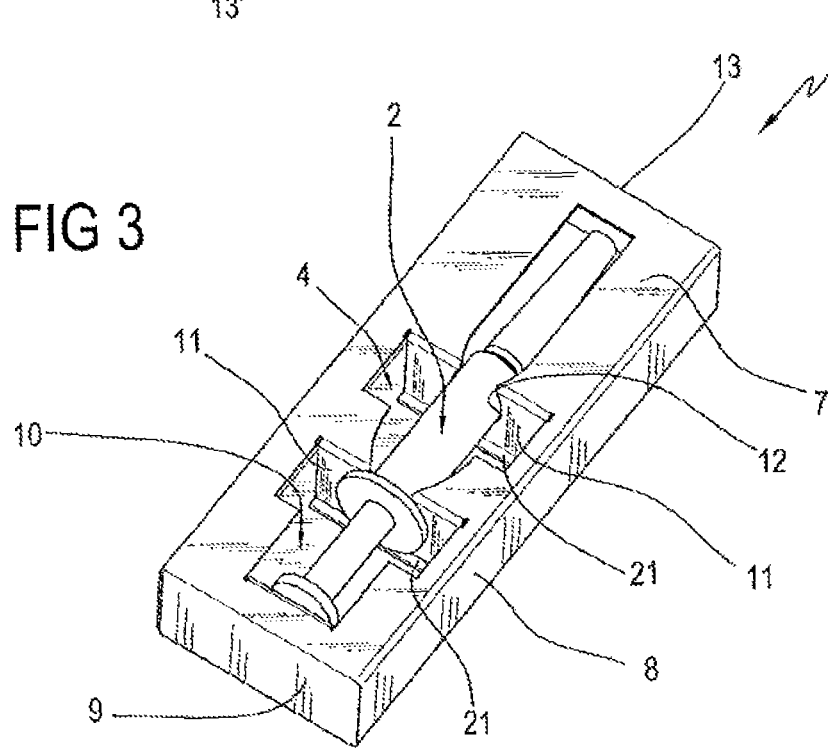
FIG. 3 is a perspective view of a second embodiment of a package for pharmaceutical products in accordance with this invention.

For example, FIG. 3 shows by way of example a second embodiment in which the supporting body 3 has a single containment compartment 4 for a respective syringe 2.

In more detail, the supporting body 3 is preferably made of paper-based material, and is switched to an operating condition in which it is substantially box-shaped (FIG. 1) and to a non-operating condition in which it has a planar profile (FIG. 2).

It should be noticed that in the operating condition the supporting body 3 is designed to contain the syringe 2 and the ampoule 5.

In contrast, in the non-operating condition, appropriately designed for storage conditions, the dimensions of the supporting body 3 are minimised.

As already indicated, the supporting body 3 is made of paper-based material so that it can easily be switched between the operating and non-operating conditions by automated folding.

In the operating condition, illustrated in detail in FIG. 1, the supporting body 3 has the shape of a parallelepiped with a rectangular base forming a base face 6 and an upper face 7 which is opposite and parallel with the base face 6.

The base face 6 and the upper face 7 are connected to each other by two lateral walls 8, or lateral faces 8, extending perpendicularly to the faces 6, 7. There are also two end faces 9, that is to say, another two lateral faces 9, also opposite each other and extending at the ends of the lateral walls 8.

Each containment compartment 4 is made in the upper face 7 and is formed by a respective opening 10.

More particularly, the upper face 7 is cut to form the openings 10 according to the number and shape of the products 2 which must be supported.

The upper face 7 also comprises at least one tab 11 extending, in the operating condition illustrated in FIGS. 1 and 2, inside the supporting body 3.

In other words, the upper face 7 comprises at least one tab 11, which forms a foldable portion 11 defined by cutting lines 17 of the upper face 7 and/or by crease lines 15.

Once the supporting body 3 is switched to its final box shape, the tab 11 is decisive for creating a contact when the parenteral product is inserted in the containment compartment 4. The tab 11 forms a load-bearing structure of the supporting body 3 which therefore is not deformed by pressing when the parenteral product (2, 5) is inserted in the containment compartment 4.

The foldable portion 11 delimits the opening 10.

The tab 11 comprises a recess 12 forming a cavity 12 for receiving, for example but without limiting the scope of the invention, the syringe 2 or the ampoule 5.

The cavity 12 is formed by a portion of the edges of the opening 10.

The recess 12 is designed to retain the product 2, removably constraining it to the supporting body 3.

In this situation it should be noticed that the syringe 2 and the ampoule 5 in the example illustrated are housed in the containment compartment 4 within the volumetric dimensions of the body 3.

FIG. 2 shows the body 3 in the non-operating condition, in which the tabs 11 are folded flat inside the respective openings 10.

In other words, in the non-operating condition, the tabs 11 are coplanar with the upper face 7.

Also with reference to FIG. 2, it should be noticed that in the minimum dimensions configuration (non-operating condition) the upper face 7 and the base face 6 of the supporting body 3 are positioned in such a way that they are against each other and superposed. In this situation, both of the faces 6, 7 form a planar profile to eliminate the height dimension of the body 3.

Said minimum dimensions configuration is obtained by folding the body 3 flat on itself using suitable crease lines 13 which divide the faces 6, 7 from the lateral walls 8.

In this way, even the end faces 9 are extended outside the body 3 so that the entire supporting body 3 can lie flat in the minimum dimensions condition.

As shown in FIG. 4, the supporting body 3 is made from a flat blank 14 obtained from a single sheet.

The blank 14 is suitably shaped and comprises a set of crease lines 13 so that it can be folded on itself.

The crease lines 13 define in the blank the upper face 7, the base face 6 and the lateral faces (8, 9).

In this way, by means of suitable steps of folding and gluing the opposite edges of the blank 14, the body 3 is formed.

The foldable portion 11 of the upper surface 7 comprises a band 21 which can be further folded relative to a crease line 20 made at the portion 11.

The band 21 defines a part of the portion 11 designed to be folded at the same time as the portion 11 is folded towards the inside of the supporting body 3.

The band 21 is configured to make contact with and superpose the base surface 6 in the blank 14 operating condition.

In FIGS. 1 and 3 in which the blank 14 is in the operating configuration, the band 21 has been folded in such a way that it projects inside the containment compartment 4.

In FIG. 6, showing an alternative embodiment to the embodiments in FIGS. 1 and 3, the band 21 is folded so that it projects towards the outside of the containment compartment 4.

In particular, the band 21 is fixed to the base wall 6 by a layer 19 of glue.

It should be noted that gluing the band 21 to the base wall 6 allows the body 3 to be stiffened in the operating configuration.

Thus, the portion 11 advantageously allows the body 3 to be reinforced since it forms a vertical stiffening wall interposed between the upper face 7 and the base wall 6.

In FIG. 7a the tab 11 does not comprise the band 21, but is shaped with a projecting portion 7s of smaller width 7L. In that alternative embodiment, the tab 11, when folded towards the inside of the supporting body 3, lodges in a notch 28 made in the base face 6. The depth P of the projecting portion 7s is less than the depth P1 of the notch 28 so that the tab 11 juts out relative to the base face 6.

Therefore, when it is lodged in the notch in the base face 6, the tab 11 is stably positioned relative to the base face 6.

Advantageously, in the non-operating condition, the body 3 can be stored in a respective minimum dimensions configuration in which it is flattened.

In this way, once formed from the blank 14, the body 3 is stored and its volumetric dimensions are significantly limited. It should also be noticed that in this configuration, the body 3 can be stacked on other bodies 3 waiting to be configured in the operating condition.

When a product needs packaging, for example a disposable product, the body 3 is switched to the operating condition by moving the faces 6, 7 away from each other to form the box-shaped configuration. In this situation the lateral walls 8, the tabs 11 and the end faces 9 are angled so that they are perpendicular to the faces 6, 7, thus forming the containment compartments 4 for the syringe 2 and/or the ampoule 4 in the example.

It should be considered that the package significantly limits the dimensions of the structure of the body 3, particularly in the non-operating conditions in which the package is stored in the warehouse.

Even the steps of making the package are particularly simple and inexpensive. The body 3 is formed by means of a simple step of folding the blank 14 and therefore does not require complex, expensive equipment.

It shall be understood that the examples described with reference to FIGS. 1, 2 and 4 and to FIG. 3 are provided by way of example only and do not limit the scope of the invention.

In light of this, the package 1 may be configured to contain any number of pharmaceutical products, in different compartments 4 or in the same compartment 4 as shown for example in FIGS. 8, 9, 10 and 11.

Said alternative embodiments, which do not depart from the inventive scope of this invention, are not described in further detail.

FIG. 5 shows an alternative embodiment of the package of FIGS. 1, 2 and 3.

In accordance with that alternative embodiment, the base face 6 has a plurality of pre-weakened tear lines made in it.

The pre-weakened tear lines define a foldable portion 18 of the base face 6. In other words, it is possible to tear the base face 6 at the pre-weakened tear lines to detach a portion 18 of the base face 6 and fold it towards the inside of the supporting body 3.

Alternatively, the portion 18 can be made by means of cutting lines made using known techniques.

The advantageous technical effects associated with the alternative embodiment illustrated in FIG. 6 are described below.

As shown in FIG. 5, the portion 18 is folded towards the upper face 7 when the foldable portion 11 has been folded towards the base face 6.

In light of this, the portion 18 forms a constraint for the portion 11 of the upper face 7 which prevents the portion 11 of the upper face 7 from returning to the position coplanar with the remaining surface of the upper face 7.

When it is folded towards the inside of the supporting body 3, the portion 18 prevents the foldable portion 11 from performing any further rotation in the direction labelled W. This prevents an elastic effect from making the portion 11 return coplanar with the upper face 7.

One advantage of this invention is that makes available a package for pharmaceutical products, in particular for syringes and/or ampoules, which is easy and inexpensive to make.

The package is advantageously made from a single blank, preferably made of paper-based material, by making a plurality of crease lines for making the folding lines of the lateral faces, of the upper face and of the base face.

In addition, the opening and the foldable portion of the upper face, which are made in a simple way, for example by punching or using known techniques, allow allow a housing and a cavity for retaining the pharmaceutical product to be formed.

The foldable portion is made at the opening in such a way that a segment of its edge forms the cavity of the foldable portion designed to removably retain the pharmaceutical product in the compartment. This means that at the same time as the opening is made, it is also possible to rapidly and practically make the cavity of the foldable portion for retaining the product.

The access opening designed to receive the syringe is formed by the same opening and by the foldable portion, which when folded towards the inside of the containment body forms another opening, adjacent to the opening 10, corresponding to the plan view surface that the mobile portion occupies when it is planar with the rest of the surface of the upper face.

The above description defines a method for making a package for pharmaceutical products.

According to the invention the method comprises the steps of:

preparing a blank 14, preferably made of paper-based material;

making a plurality of crease lines 13 in the blank 14 to define a base face 6, an upper face 7, and a plurality of lateral faces 8;

making at least one opening 10 in the upper face 7;

making cutting lines 17 and/or additional crease lines 15 in the upper face 7 for defining a foldable portion 11 of the upper face 7 which partly delimits the opening 10 for forming a cavity 12 for retaining the product.

The method also comprises the following additional steps:

folding the lateral faces 8 at the crease lines 13 to give the blank 14 a box shape and form a supporting body 3;

removably constraining the upper face 7, the base face 6 and the lateral faces 8 to each other;

folding the foldable portion 11 of the upper face 7 towards the inside of the supporting body 3 to form, at the opening 10, a compartment 4 for containing the pharmaceutical products.

Preferably, according to the method, after the step of folding the foldable portion 11 of the upper face 7 towards the base face 6, there is a step of using a layer 19 of glue to fix the foldable portion 11 to the base face 6.

Alternatively to gluing, the following is possible:

making pre-weakened tear lines in the base face 6 for defining a portion 18 of the base face 6 which can be folded towards the inside of the supporting body 3;

folding the portion 18 of the base face 6 which can be folded towards the inside of the supporting body 3, after the foldable portion 11 of the upper face 7 has been folded towards the inside of the supporting body 3, for constraining the foldable portion 11 of the upper face 7.

According to this aspect, the portion 18 of the base face 6 prevents rotation of the portion 11 of the upper face 7 in the direction W.

Figure 8:
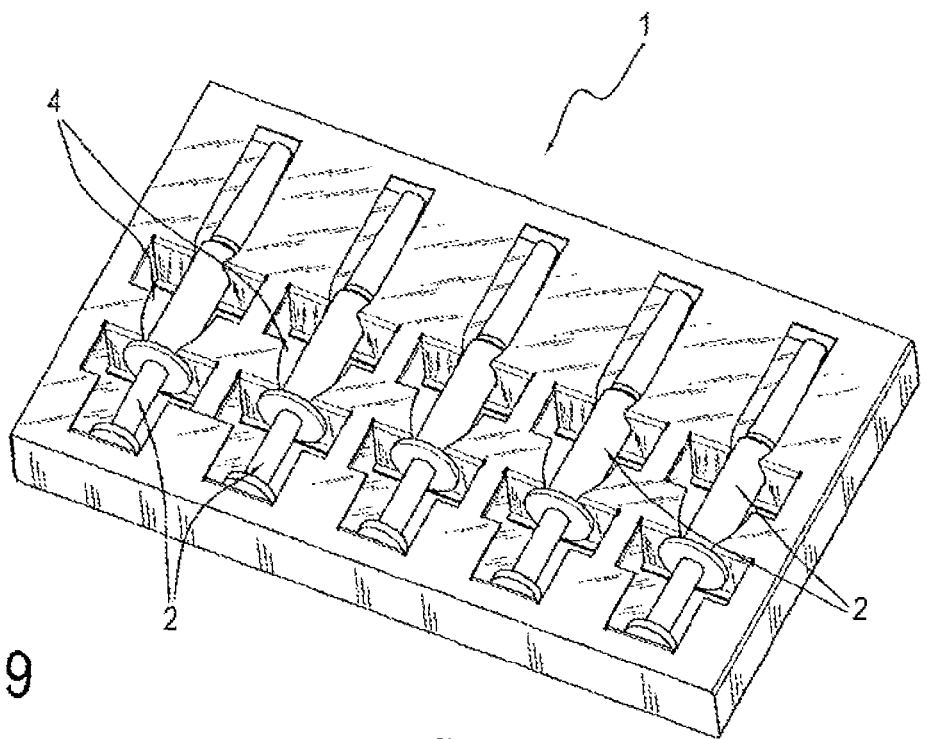
FIG. 8 is a perspective view of a package for pharmaceutical products containing a plurality of syringes.
Figure 9:
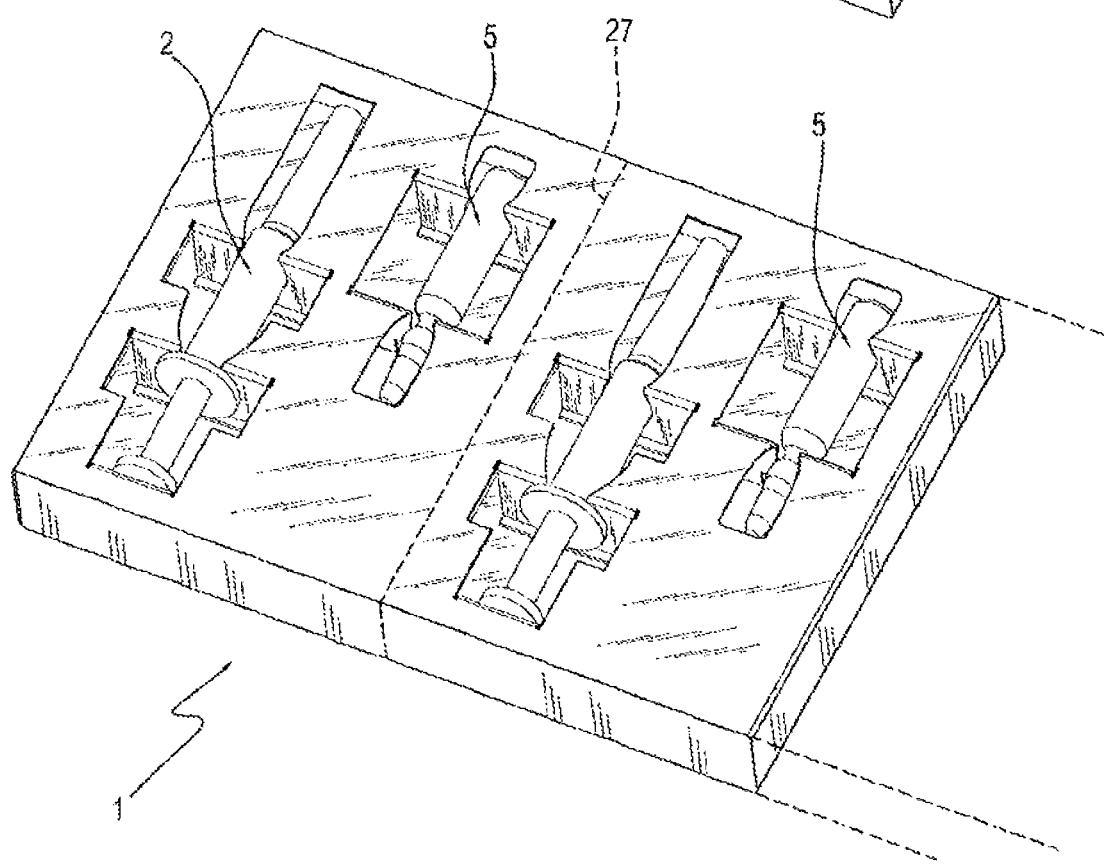
FIG. 9 is a perspective view of a package for pharmaceutical products containing a plurality of syringes and respective filling ampoules.

FIGS. 8 and 9 show a package 1 comprising a plurality of containment compartments 4.

In particular, FIG. 8 shows a package 1 containing a plurality of syringes 2.

In contrast, FIG. 9 shows a package 1 containing a plurality of syringes 2 with respective ampoules 5.

Preferably, in accordance with the embodiment illustrated in FIG. 9, the numeral 27 denotes a pre-weakened tear line of the supporting body 3 for dividing the supporting body 3 into different portions, each containing a syringe 2 and the respective ampoule 5 for filling it.

Advantageously, according to that aspect, the user can detach a portion of the supporting body 3 containing a syringe 2-ampoule 5 set.

Figure 10:
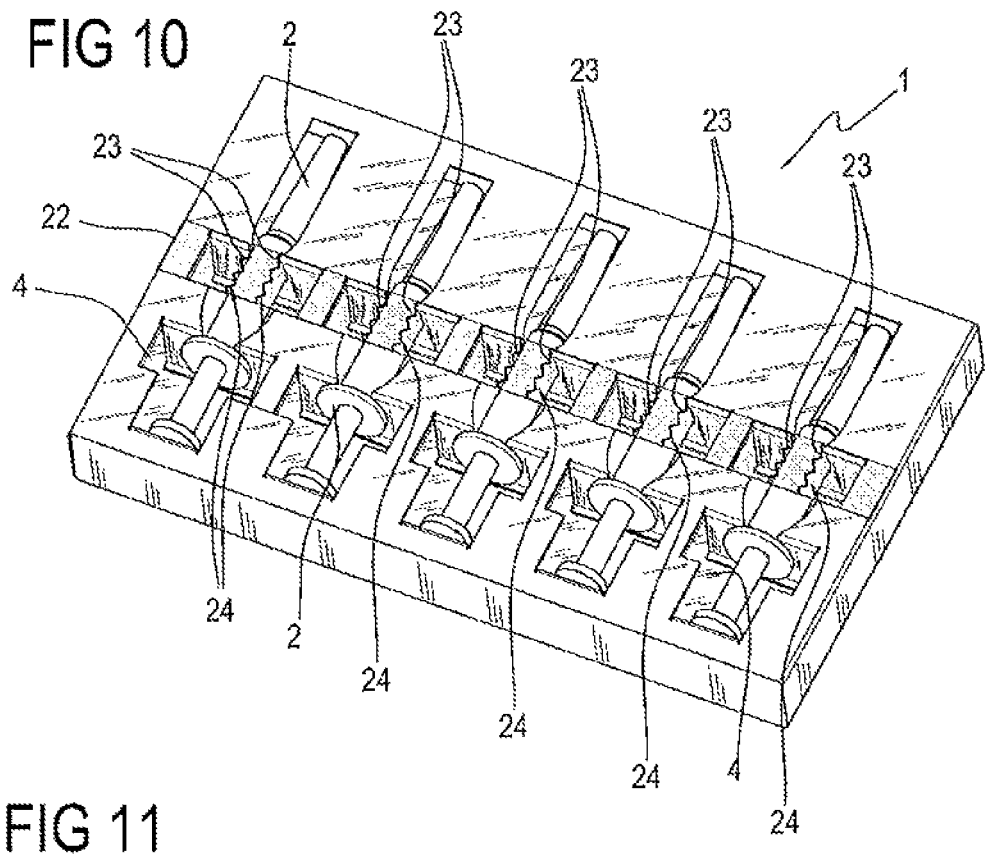
FIG. 10 is a perspective view of a package for pharmaceutical products containing a plurality of syringes with a tamper-evident device.
Figure 11:
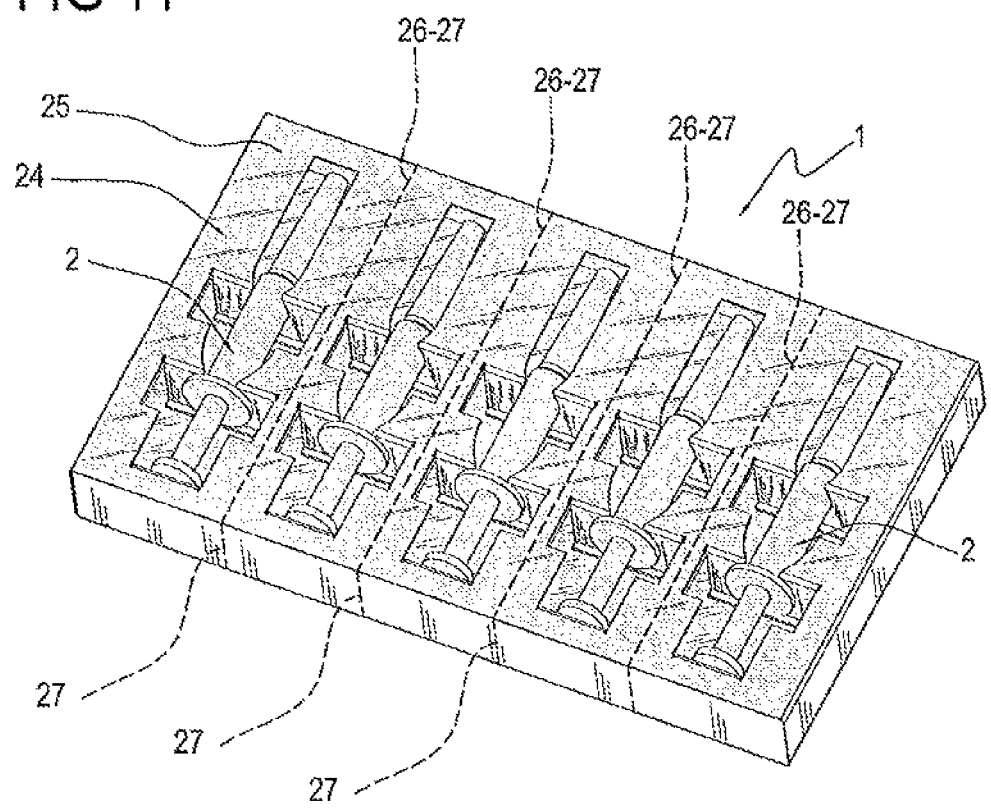
FIG. 11 is a perspective view of a package for pharmaceutical products containing a plurality of pharmaceutical products with a tamper-evident device.

According to another aspect of the invention, illustrated in FIGS. 10 and 11, after the package 1 has been brought to its final box shape and the parenteral products 2, 5 have been inserted in the respective containment compartment, if necessary, the package 1 is completed by applying a tamper-evident seal 24 for the package 1.

The tamper-evident seal 24 forms means 24 for indicating that the package 1 or any part of the package 1 has not been opened.

By way of example, but without limiting the scope of the invention, the tamper-evident means 24 may be made of material, mainly but not exclusively paper-based material, which is applied by heat-sealing, gluing or in self-adhesive fashion to the package 1 after the parenteral products (2, 5) have been inserted in the respective containment compartment 4.

The tamper-evident means 24 guarantee that the parenteral products 2, 5 have not been removed from the containment compartment 4 after application of the means 24 to the package.

A break in the tamper-evident means 24, meaning that the means 24 are not whole, indicates that the parenteral product 2, 5 has been removed from the containment compartment 4 after application of the tamper-evident means 24. In this sense, the tamper-evident means 24 increase the security of the package 1 because they prevent unauthorised persons from opening the package 1, handling the contents and altering them, then closing the package 1 again without the end user of the package having any way of knowing that this has been done.

As illustrated in FIG. 10, the tamper-evident means comprise a label 22 designed to simultaneously seal a plurality of containment compartments 4.

Alternatively, according to an embodiment not illustrated, there may be one label 22 for each containment compartment 4, configured to preferably partly, or alternatively completely, block access to the containment compartment 4 so that the parenteral product cannot be removed from the compartment 4 without the label 22 at least partly tearing.

The label 22 is preferably a self-adhesive label.

The label 22 preferably bears indications about the parenteral product (2, 5) contained in the containment compartment 4.

The label 22 is applied to the package 1 by the pharmaceutical company responsible for packaging after the respective product 2 has been inserted in the containment compartment 4.

The label 22 has tear lines 23 so that it tears at said tear lines 23 if the respective parenteral product 2 is removed from the containment compartment 4.

Alternatively, the package 1 tamper-evident means 24 comprise a sheet 25, preferably semi-transparent, fixed to the package (as shown in FIG. 11).

The sheet 25 is preferably heat-sealed to the package 1.

The heat-sealed sheet 25 is applied to the package 1 by the pharmaceutical company responsible for packaging after the respective products 2 have been inserted in the containment compartment 4.

The sheet 25 has pre-weakened tear lines 26 which define portions of the sheet 25 relative to a compartment 4 which are designed to tear at the respective pre-weakened tear lines 26 if the product 2 is removed from the compartment 4.

If the package 1 is completely covered, that is to say, if the tamper-evident means 24 cover the entire package 1, the tamper-evident seal 24 is applied as follows:

by heat-sealing due to paints present both on the outside of the supporting body 3 switched to the final box shape and on the lower face of the tamper-evident means 24 designed to be placed in contact with the body;

by application of glue on one of the two faces, that is to say, on the face of the means 24 or on the face of the supporting body 3, which make contact, before application of the paper cover.

In both cases, the cover for the package 1 of parenteral products (2, 5) may be complete or partial.

Figure 12:
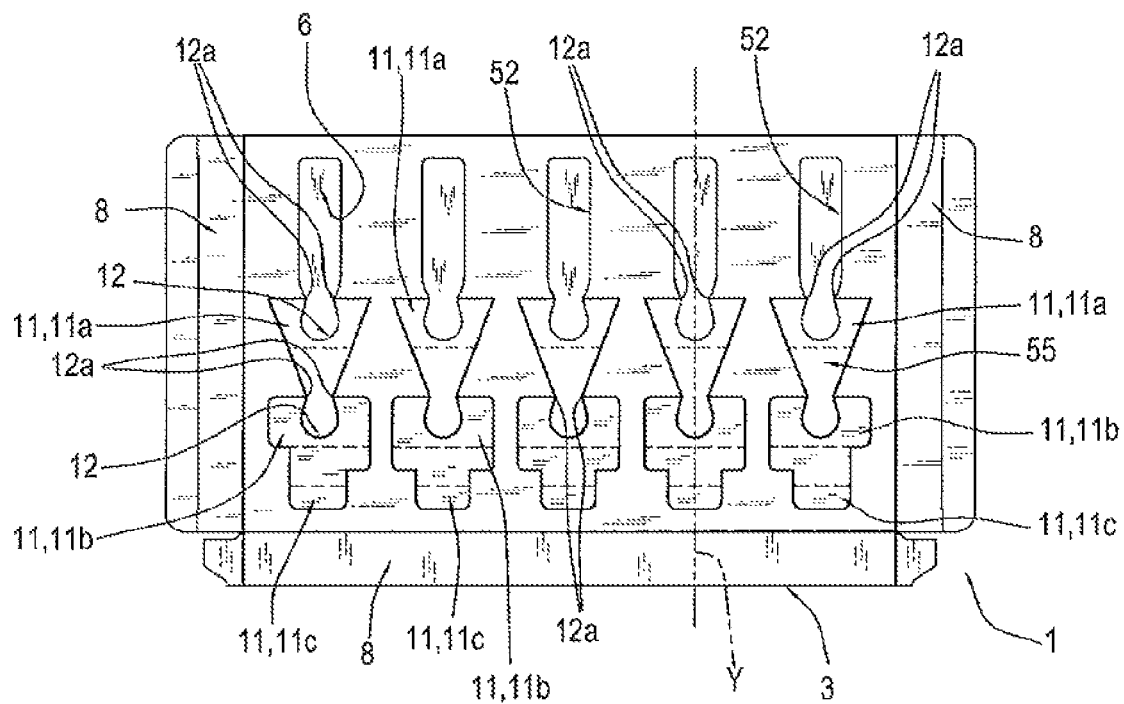
FIGS. 12 to 14 are plan and perspective views of an alternative embodiment of the package for pharmaceutical products according to the invention in different configurations.
Figure 13:
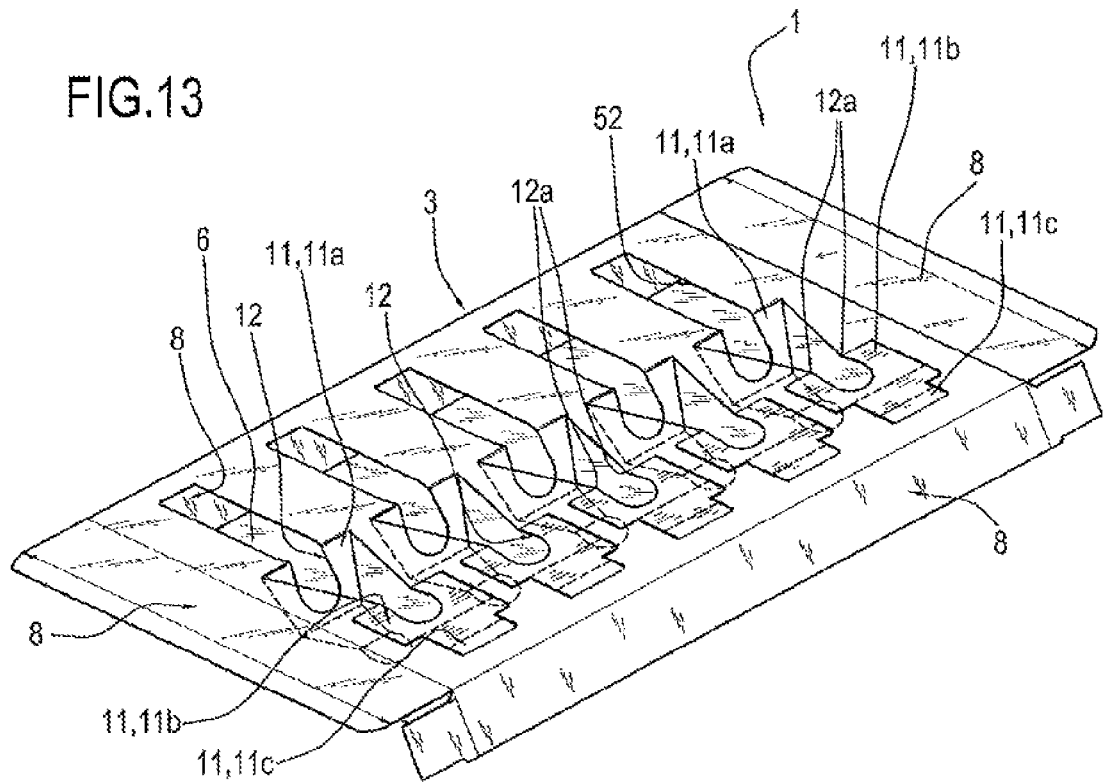
Figure 14:
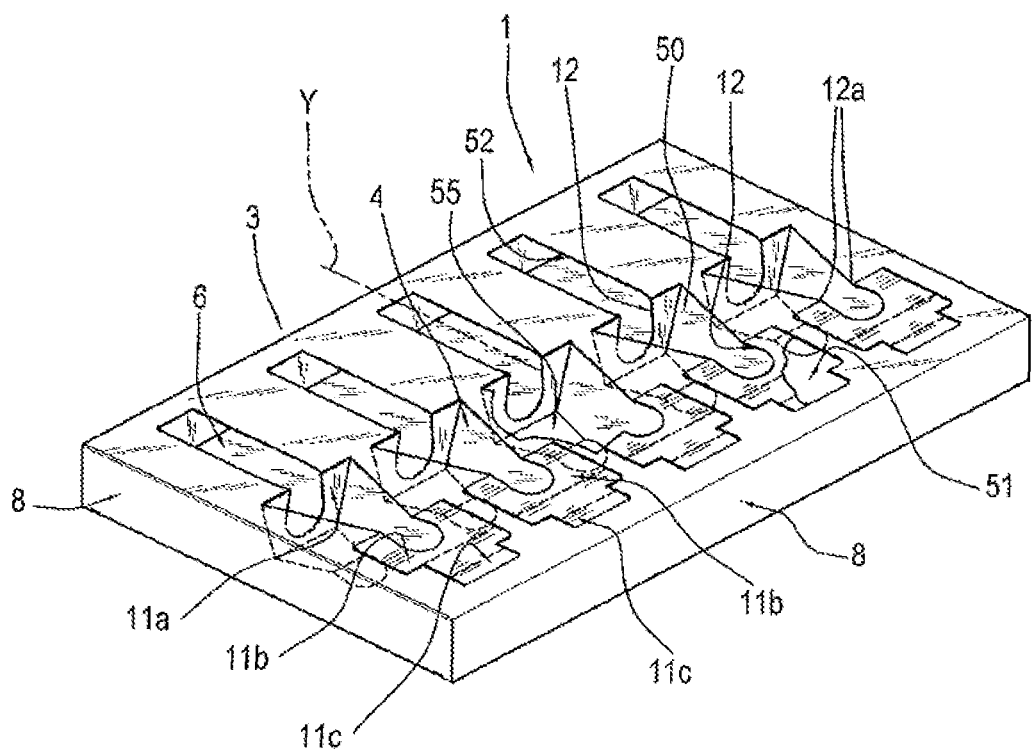

FIGS. 12 to 14 illustrate yet another embodiment of the package 1 according to the invention.

More specifically, FIG. 12 shows the package 1 with the body 3 in a substantially planar configuration of minimum dimensions (that is, in the non-operating configuration), FIG. 13 shows the package 1 partly erected whilst FIG. 14 shows the package 1 fully erected (that s, in the operating configuration).

It should be noted that the package 1 comprises a pair of foldable portions (or tabs) 11 (labelled individually 11a and 11b), forming a cavity 12 for receiving the product, and a further foldable portion (or tab) 11c (which does not form a cavity for receiving the product).

More specifically, it should be noted that folding the first tab 11a inwards forms an opening 50, whilst folding the second tab 11b inwards forms a further opening 51.

The reference numeral 52 denotes an opening in the surface 6, obtained by blanking.

The openings 50 and 51 form a portion of the compartment 4 (the compartment 4 as a whole is formed by the openings 50. 51 and 52).

It should be noted that the syringe is inserted into the compartment 4 when the body 3 has been shaped into the operating configuration, resting on the cavities 12 of the first tab 11a and of the second tab 11b. Thus, the syringe 2 is suspended relative to the base wall 6

This guarantees that the syringe 2 is held securely in the package 1 because the syringe is held within the cavities 12

Further, to ensure that the syringe is held even more securely, the cavity 12 comprises a constriction 12a that effectively and securely holds the syringe 2 within it. In effect, when the syringe 2 is inserted into the package 1, the constriction 12a prevents the syringe 2 from accidentally falling out of the compartment In light of this, it should be noted that, in more general terms, the cavity 12 is shaped to hold the syringe 2 within it More specifically, it should be noted that the method for making the box 3 entails gluing a part 55 of the folding portion 11a to the base wall 6 (this part of the folding portion 11a is denoted by the reference numeral 55). This guarantees and reinforces the box 3 since the vertical wall of the tab 11a, which is fixed to the wall 6, provides structural support for the body 3 in the configuration of maximum dimensions since it is rigidly interposed between the base wall 6 and the upper face 7 of the package.

It should also be noted that, preferably, the folding portion 11c makes contact with the end of the plunger of the syringe when the latter is inserted into the cavities 12 in the compartment 4. The folding portion 11c thus prevents the syringe 2 from moving along the main direction of extension Y of the compartment 4

It should be noted that one advantage of the package 1 of this invention is that it allows the products to be held securely within it (even if the box is turned upside down, the products inside it do not fall out of the compartment 4) and at the same time the invention guarantees a package 1 with good structural rigidity.

The invention claimed is:

1. A package for a pharmaceutical product, comprising:
a supporting body forming at least one compartment for containing the pharmaceutical product, the supporting body being made from a single-sheet blank of paper-based material, and including a base face, an upper face and a plurality of lateral faces which are connected to at least one chosen from the base face and the upper face,
wherein the upper face includes at least one opening and at least one foldable portion defined by at least one chosen from cutting lines of the upper face and crease lines and delimiting a portion of the at least one opening, the at least one foldable portion including a retention cavity for receiving and retaining the pharmaceutical product,
the supporting body being switchable between a non-operating condition having a planar profile which minimises dimensions, and an operating condition in which:
the supporting body is substantially box-shaped;
the at least one foldable portion is folded inside the supporting body so that together with the at least one opening, the at least one foldable portion forms a containment compartment for containing the pharmaceutical product, the retention cavity positioned on the at least one foldable portion to removably constrain the pharmaceutical product in the containment compartment suspended away from the base wall;
wherein the containment compartment is defined by at least two openings and comprises at least two foldable portions, with one of the at least two foldable portions separating the at least two openings, the at least two foldable portions each including retention cavities for receiving and retaining the pharmaceutical product.

2. The package according to claim 1, wherein the at least two foldable portions are in contact with each other in the non-operating condition.

3. The package according to claim 1, wherein at least one of the at least two foldable portions forms a constraint in a main direction of extension of at least one of the at least two openings in the operating condition.

4. The package according to claim 1, wherein at least one of the at least two foldable portions comprises an end band contacting and superposed on a surface of the base in the operating condition.

5. The package according to claim 4, wherein the end band is positioned inside the containment compartment when it is contacting and superposed on the surface of the base in the operating condition.

6. The package according to claim 1, and further comprising a layer of glue fixing at least one of the at least two foldable portions to the surface of the base.

7. The package according to claim 1, wherein the base comprises a third foldable portion foldable towards the inside of the supporting body in the operating configuration to form a constraint for stable positioning of at least one of the at least two foldable portions of the upper face.

8. The package according to claim 1, wherein in the operating condition, the supporting body has a parallelepiped shape with a rectangular base.

9. The package according to claim 1, wherein at least one of the at least two foldable portions comprises a tab extending, in the supporting body operating condition, inside the body for supporting and retaining the pharmaceutical product.

10. The package according to claim 1, and further comprising a plurality of containment compartments; each containment compartment for containing a respective pharmaceutical product.

11. The package according to claim 1, and further comprising a tamper-evident mechanism for at least a part of the package.

12. The package according to claim 11, wherein the tamper-evident mechanism comprises at least one label which, after the pharmaceutical product has been inserted into the compartment, is positioned over the containment compartment to at least partly block access to the containment compartment, the label having tear lines for tearing upon removal of the pharmaceutical product from the containment compartment.

13. The package according to claim 11, wherein the tamper-evident mechanism comprises a sheet positioned on the upper face of the supporting body at least at the compartment and having pre-weakened tear lines, the sheet being tearable at the pre-weakened tear lines upon removal of the pharmaceutical product from the containment compartment.

14. A method for making a package for a pharmaceutical product, comprising:
preparing a single sheet blank made of paper-based material;
making a plurality of crease lines in the blank to define a base face, an upper face and a plurality of lateral faces which are connected to at least one chosen from the base face and the upper face;
making at least one opening in the upper face;
making at least one chosen from additional cutting lines and crease lines in the upper face for defining a foldable portion of the upper face partly delimiting at least a portion of the at least one opening, the foldable portion including a retention cavity for receiving and retaining the pharmaceutical product,
moving the supporting body from a non-operating condition having a planar profile which minimises dimensions to an operating condition in which:
the supporting body is substantially box-shaped;
the foldable portion is folded inside the supporting body so that together with the at least one opening, the foldable portion forms a containment compartment for containing the pharmaceutical product,
positioning the retention cavity on the foldable portion to removably constrain the pharmaceutical product in the containment compartment suspended away from the base wall when the foldable portion is folded towards the inside of the supporting body;
wherein the containment compartment is defined by at least two openings and comprises at least two foldable portions, with one of the at least two foldable portions separating the at least two openings, the at least two foldable portions each including retention cavities for receiving and retaining the pharmaceutical product.

15. The method according to claim 14, further comprising, fixing the at least one of the at least two foldable portions to the base face using a layer of glue.

16. The method according to claim 14, and further comprising:
making pre-weakened tear lines in the base face for defining a portion of the base face which can be folded towards the inside of the supporting body;
folding the portion of the base face which can be folded towards the inside of the supporting body, after the at least two foldable portions of the upper face have been folded towards the inside of the supporting body, for constraining and stably positioning at least one of the at least two foldable portions of the upper face.

17. The method according to claim 14, comprising, one after another: inserting the pharmaceutical product in the containment compartment; and applying a tamper-evident seal to at least a portion of the package containing the pharmaceutical product.

18. The method according to claim 17, wherein the tamper-evident seal is made of a material which is mainly paper which is glued or heat-sealed on the upper face of the package containing the pharmaceutical product.

19. The method according to claim 17, wherein the tamper-evident seal comprises tear lines for tearing if the pharmaceutical product is removed from the containment compartment.

20. The method according to claim 17, wherein the tamper-evident seal is a self-adhesive label bearing indications about the pharmaceutical product contained in the containment compartment.

21. A package for a pharmaceutical product, comprising:
a supporting body forming at least one compartment for containing the pharmaceutical product, the supporting body being made from a single-sheet blank of paper-based material, and including a base face, an upper face and a plurality of lateral faces which are connected to at least one chosen from the base face and the upper face,
wherein the upper face includes at least one opening and at least one foldable portion defined by at least one chosen from cutting lines of the upper face and crease lines and delimiting a portion of the at least one opening, the at least one foldable portion including a retention cavity for receiving and retaining the pharmaceutical product,
the supporting body being switchable between a non-operating condition having a planar profile which minimises dimensions, and an operating condition in which:
the supporting body is substantially box-shaped;

the at least one foldable portion is folded inside the supporting body so that together with the at least one opening, the at least one foldable portion forms a containment compartment for containing the pharmaceutical product, the retention cavity positioned on the at least one foldable portion to removably constrain the pharmaceutical product in the containment compartment suspended away from the base wall;

wherein the containment compartment is formed by at least two openings and comprises at least two foldable portions, the at least two foldable portions being placed in contact with each other in the non-operating condition.

\* \* \* \* \*